United States Patent [19]

Reese et al.

[11] Patent Number: 5,008,198

[45] Date of Patent: Apr. 16, 1991

[54] MEROZOITE SURFACE GLYCOPROTEINS

[75] Inventors: Robert T. Reese, San Diego; Harold A. Stanley, La Jolla, both of Calif.

[73] Assignee: Scripps Clinic and Research Foundation, La Jolla, Calif.

[21] Appl. No.: 358,663

[22] Filed: May 30, 1989

Related U.S. Application Data

[62] Division of Ser. No. 650,810, Sep. 14, 1984, Pat. No. 4,835,259.

[51] Int. Cl.$^5$ .................. C12N 5/00; A61K 35/14; C07K 3/00; C07K 13/00
[52] U.S. Cl. .................. 435/240.27; 530/387; 530/808; 530/809
[58] Field of Search ............... 530/350, 387; 439/240.27; 424/88

[56] References Cited

U.S. PATENT DOCUMENTS 4,835,259  5/1989  Reese et al. ............... 530/395

OTHER PUBLICATIONS

Clark, J. T. et al., Mol. and Biochem. Parasitol, 32:15–24, 1989, "46–53 KDa Glycoprotein . . . ".
Stanley, H. A. et al., PNAS (U.S.A.) 83:6093–6097, "Plasmodium Falciparu Polypeptides . . . ".
Smythe, J. A. et al., PNAS (U.S.A.):85, pp. 5195–5199, Jul. 1988, "Indentification of Two Integral . . . ".
Epping et al., Mol. Biochem. Parasitol., 28:1–10 (1988).
Pirson et al., J. Immunol., 134:1946–1951 (1985).
Perrin et al., Immunological Rev., 61:245–269 (1982).
Reese et al., Am. J. Trop. Med. Hyg., 30:1168–1178 (1981).
Perrin et al., Transactions of the Royal Society of Tropical Medicine and Hygiene, 75:163–165 (1981).
Brown et al., Nature, 297:591–593 (1982).
Myler et al., Molecular and Biochemical Parasitology, 9:37–45 (1983).
Heidrich et al., Z. Parasitenkd, 69:715–725 (1983).
Freeman et al., J. Exp. Med., 158:1647–1653 (1983).
Holder et al., J. Exp. Med., 156:1528–1538 (1982).
Hall et al., Molecular and Biochemical Parasitology, 7:247–265 (1983).
Howard et al., Molecular and Biochemical Parasitology, 10:319–334 (1984).
Howard et al., Malaria and the Red Cell, John Eaton, ed., pp. 45–61 (1984).
Dubois et al., Proc. Natl. Acad. Sci. U.S.A., 81:229–232 (1984).
Holder et al., J. Exp. Med., 160:624–629 (1984).
Perkins, Molecular Biochemical Parasitology, 5:55–64 (1982).
Kilejian, Proc. Natl. Acad. Sci. U.S.A., 77:3695–3699 (1980).
Miller et al., Journal of Immunology, 114:1237–1242 (1975).

Primary Examiner—Margaret Moskowitz
Assistant Examiner—T. Cunningham
Attorney, Agent, or Firm—Dressler, Goldsmith, Shore, Sutker & Milnamow, Ltd.

[57] ABSTRACT

The invention comprises antigenic glycoproteins substantially similar to antigenic glycoproteins present on the surface of the merozoite form of Plasmodium falciparum, including glycoproteins of molecular weights of about 56,000 present in the Geneva and FVO isolates and about 50,000 that is present in the Honduras I/CDC, Indochina 1, Kenya and Tanzania I isolates. The invention also comprises monoclonal antibodies 4-8-5D (HB 8938) which bind to the 56,000 glycoprotein of the invention, a hybridoma cell line that is capable of producing these monoclonal antibodies, and vaccines and vaccine compositions comprising these glycoproteins or epitopes substantially similar to or cross reactive with these glycoproteins or genes or gene fragments encoding such epitopes.

2 Claims, No Drawings

MEROZOITE SURFACE GLYCOPROTEINS

The invention described herein was made in the course of work under Contract DPE-0453-C-00-1017-00 from the U.S. Agency for International Development.

This is a division of application Ser. No. 650,810, filed Sept. 14, 1984, now U.S. Pat. No. 4,835,259.

This invention relates to antigenic compounds found in malarial parasites and to their isolation and use. In particular the invention relates to antigenic glycoproteins present in *Plasmodium falciparum* merozoites. The invention also relates to corresponding monoclonal antibodies and hybridoma cell lines, and to vaccines comprising the antigenic glycoproteins.

Malaria is currently the most prevalent death-threatening infectious disease in the world. Malaria is predominantly a problem in developing nations; thus, if a vaccine could be produced, it would be likely to have dramatic effects on the general health and productivity of these people. Although accurate statistics are not readily available, there are likely to be 300–500 million cases of malaria per year. Approximately 1% result in death, the rest (297–495 million) have varying degrees of illness which on the average claim one or more weeks of effective work time, even among the educated who are properly diagnosed and treated. Thus, the morbidity due to this disease is even more devastating to the economy of these countries than is the mortality.

For the elimination of the asexual blood stages of the human malarial parasite *Plasmodium falciparum* it is necessary for the immune response to recognize antigens, including modified or unmasked antigens, found at the surface of either the parasitized erythrocyte or the extracellular merozoite. The importance of merozoite surface antigens has been indicated by in vitro assays which suggest that antibodies to these antigens can block the merozoites from binding to and penetrating erythrocytes.

Several approaches have been used to directly and indirectly investigate the polypeptide composition of the merozoite. Metabolically labeled parasites have been immunoprecipitated with immune sera which inhibit the growth of the parasite in vitro. By comparing these results to those obtained with noninhibiting sera, and assuming that the inhibition observed in such an assay is due to antibody binding to merozoites and not to infected erythrocyte surfaces, Reese et al., *Am. J. Trop. Med. Hyg.* 30:1168 (1981) showed that the ability to inhibit parasite growth in vitro correlated with the ability to immunoprecipitate proteins of relative molecular weights ($M_r$) of approximately 200K, (that is, 200,000), 70-85K, and 45K. Comparable results were obtained by Perrin and Dayal, *Immunological Rev.* 61:245 (1982), and Perrin et al., *Trans. Roy. Soc. Trop. Med. Hyg.* 75:163 (1981) except that they also identified two additional proteins of approximate $M_r$ 140K and 110K. Conversely, Brown et al., *Nature* 279:591 (1982), using a similar technique were able to identify only one such protein (approximate $M_r$ 96K).

A second way of investigating the polypeptide composition of the merozoites is to metabolically label parasites late in the cell cycle and to note which labeled proteins are still present in the ring states after reinvasion. Using such a procedure Myler et al., *Mol. Biochem. Parasitol.* 9:37 (1983), identified fifteen $^{35}$S-methionine-labeled merozoite proteins (approximate $M_r$ 240–14K). Heidrich et al., *Z. Parasitenkd.* 69:715 (1983), identified six merozoite "surface" antigens (approximate $M_r$ 81K, 38K, 35K, 20K, and 12K) while Freeman and Holder *J. Exp. Med.* 158:1647 (1983), have identified eleven such proteins (approximate $M_r$ 160K, 105K, 83K, 73K, 70K, 65K, 48K, 42K, 41K, 38K, and 37K).

Finally, monoclonal antibodies (McAb's), which react with what appear by immunofluorescence to be merozoites, have been used to immunoprecipitate antigens from metabolically-labeled parasites. Using this approach Perrin and Dayal, (1982), supra, described at least three proteins (approximate $M_r$ 140K, 82K, and 41K), Howard et al. three proteins (approximate $M_r$ 82K, 39K and 37K), Hall et al., *Mol. Biochem. Parasitol.* 7:247 (1983), two proteins (approximate $M_r$ 190K and 160K), and Holder and Freeman *J. Exp. Med.* 156:1528(1982), one protein (approximate $M_r$ 83K), which they believe to be merozoite associated.

The invention comprises a class of antigenic glycoproteins, in essentially pure form, substantially similar to or derived from antigenic glycoproteins present on the surface of *Plasmodium falciparum*, in particular on the surface of the merozoite form of *P. falciparum*. For present purposes, a glycoprotein is "substantially similar" to another glycoprotein where their amino acid sequences are substantially the same and where the "glyco", or sugar parts, are substantially the same. This class of glycoproteins includes glycoproteins of molecular weights of approximately 185K, 88K, 56K, 46K and 34K, as present in isolates of *P. falciparum*. The class also includes an approximately 50K glycoprotein which appears in some isolates instead of the 56K glycoprotein in other isolates. The 56K and 50K glycoproteins are of particular importance to this invention as antigens.

The invention also comprises monoclonal antibodies (McAb's) which bind to the glycoproteins of the invention; hybridoma cell lines which are capable of producing these monoclonal antibodies; and vaccines and vaccine compositions comprising these glycoproteins or epitopes substantially similar to or cross reactive with these glycoproteins or genes or gene fragments encoding such epitopes. Physiologically acceptable adjuvants or carriers may also comprise part of the vaccines or vaccine compositions.

Methods of preparing parasite cultures and hybridomas for use with the present invention and procedures for electron microscopy and immunoprecipitation are described below, followed by the results of experiments.

Parasites

The *Plasmodium falciparum* isolates FVO (Vietnam), Indochina I (Vietnam), Honduras I/CDC (Central America), Geneva (Senegal, West Africa), Kenya (East Africa), and Tanzania I (East Africa) were cultured using standard procedures (Trager and Jensen, *Science* 193:673 (1976)). Cultures of these isolates are available. To obtain material enriched for segmenters and merozoites, the cultures were treated with Physiogel (Reese et. al., *Bull. WHO* 57 (suppl. 1):53 (1979)) when most of the parasites were early trophozoites. The infected erythrocytes (about 50-70% parasitemia) were then returned to culture (0.5% hematocrit) for 18 hr. Segments and free merozoites were harvested, washed twice with RPMI-1640 medium containing 25 mM HEPES (RPMI), and used as follows: 1) frozen at −70° C. for subsequent enzyme-linked immunosorbent assays (ELISAs), 2) smeared on slides and acetone fixed for indirect fluorescence antibody tests (IFAT), 3) repeatedly frozen and thawed for mouse immunizations.

Hybridomas

Balb/c ByJ mice were injected eight times at weekly intervals with FVO parasite material corresponding to $10^6$–$10^7$ infected erythrocytes. Three days after the final injection the splenocytes ($10^8$ cells) from one mouse were fused with an equal number of P3-X63-Ag8 myeloma cells using polyethylene glycol and standard methodology (Kohler and Milstein, Nature 245:495 (1975)). The fused cells, in Dulbecco's medium supplemented with hypoxanthine, aminopterin and thymidine and 10% (v/v) fetal bovine serum (FBS), were then placed in twenty-five 96-well tissue-culture plates using Balb/c ByJ thymocytes as a feeder layer. The cells from wells in which hybridomas grew were subcultured and the spent medium assayed by ELISA using malarial antigen attached to 96-well tissue culture plates and an alkaline phosphatase-conjugated goat anti-mouse Ig (Tago, Burligame, CA). The media which were considered positive by ELISA were subsequently assayed by IFAT. The hybridomas producing antibodies specific for merozoites and late schizonts were cloned by limiting dilution and adapted to growth in Dulbecco's medium plus 10% gamma globulin-free horse serum. Supernatants from these cultures were then concentrated 10× using PM30 Amicon Diaflo ultra filters.

Electron Microscopy

To obtain sufficient numbers of merozoites for immunoelectron microscopy, the segmenter and merozoite enriched culture material was incubated with agitation for 2 hr at a 1% packed cell volume (PCV) in RPMI plus 20% human serum. The cultures were then centrifuged at 300 g (10 min) to remove most of the erythrocytes and then at 1300 g (10 min) to pellet the remaining merozoites. The merozoites were washed once with RPMI and fixed for 10 min with 0.075% glutaraldehyde in RPMI. After washing three times with RPMI, the cells were resuspended in the concentrated hybridoma culture supernatants and placed on ice for 15 min. They were then washed three times with RPMI and 1-2 ul PCVs were placed in 200 ul volumes of a ferritin-labeled anti-mouse Ig conjugate (Cappel, West Chester, PA) appropriately diluted in PBS containing 1% (w/v) BSA. The cells were left on ice for 15 min, washed three times with RPMI, fixed with 2% glutaraldehyde in cacodylate buffer (pH 7.3), dehydrated, and embedded in EPON 812, Uranyl acetate stained thin sections were then examined in a Hitachi HU-12A electron microscope.

Immunoprecipitation

Trophozoites were concentrated by Physiogel treatment and $2 \times 10^8$ infected cells were grown approximately 18 hr in 10 ml RPMI containing 15% human serum and 1 mCi $^3$H-glucosamine (Amersham, Arlington Heights, IL). The infected erythrocytes and free merozoites were pelleted by centrifugation at 1300 g for 10 min, diluted with PBS to a 20% PCV, and frozen at −70° C. Immediately prior to an immunoprecipitation assay the cells were solubilized at a 1% PCV in radio immunoprecipitation assay Buffer A (150 mM NaCl, 40 nM NaF, 20 mM EDTA, 2% (v/v) Trasylol, 1% Triton X-100, 1% sodium deoxycholate, 0.1% sodium dodecyl sulfate, 10 mM Tris HCl, pH 7.4, at 0° C.) and centrifuged at 100,000 g for 1 hr at 4° C. The supernatant (100 ul) was then used to resuspend 10 ul antibody-bound protein A-Sepharose, previously prepared by the methods of Schneider et al., J. Biol. Chem. 257:10766 (1982). Antibodies from Aotus monkeys (karyotype VI) immune to the FVO isolate of P. falciparum had been covalently bound directly to the protein A-Sepharose while the hybridoma antibodies were indirectly bound using affinity purified polyvalent rabbit anti-mouse Ig antibody (Tago, Burlingame, CA). The antibody-bound protein A-Sepharose was incubated in the antigen solution for 1 hr (4° C.). The protein A-Sepharose-linked immune complexes were then washed twice with 0.75 ml Buffer A, once with 0.75 ml Buffer A containing 500 mM NaCl, and once with distilled water. The antigen was dissociated by boiling in sample buffer. Samples were then electrophoresed in parallel with $^{14}$C-labeled molecular weight marker proteins on 9% acrylamide gels containing sodium dodecyl sulfate.

Hybridomas were produced which produces antibodies specific for P. falciparum merozoites. The monoclonal antibodies which reacted with, that is, bound to or immunoprecipitated, merozoites from the FVO isolate gave two distinctly different fluorescence patterns. The first pattern (typified by McAb 4-10-2A), appeared as two closely associated intense fluorescent spots localized within a region of the merozoite separate from the nucleus. The second pattern (obtained with McAb's 4-8-5D and 4-13-4B) is characterized by a bright fluorescence surrounding each merozoite and would appear to be due to antibodies bound to the merozoite surface. However, since fluorescence microscopy on acetone-fixed parasites alone is inadequate to unequivocally localize the antigens, immunoelectron microscopy was employed. The results demonstrate that McAb's 4-8-5D and 4-13-4B bound to the merozoite surface while McAb 4-10-2A did not bind to the surface.

To determine the isolate specificity of McAb's 4-8-5D and 4-13-4B, parasites from five different areas were examined by IFAT and one (Honduras I/CDC) was also examined by immunoelectron microscopy. While McAb 4-13-4B reacted by IFAT with the Honduras I/CDC isolate and most of the other isolates, McAb 4-8-5D only reacted b IFAT with the FVO and Geneva isolates. The inability of McAb 4-8-5D to bind efficiently to the Honduras I/CDC isolate was subsequently confirmed by immunoelectron microscopy. In this experiment McAb 4-13-4B was used as a positive control to demonstrate that the Honduras I/CDC merozoites contained other surface antigens even though they lacked or contained significantly lower amounts of the antigen to which the McAb 4-8-5D binds.

Immunoprecipitation assays were conducted to characterize the molecules with which McAb 4-8-5D reacted. When $^3$H-glucosamine-labeled FVO or Geneva parasites were employed as antigen, McAb 4-8-5D immunoprecipitated a single molecule of approximate $M_r$ 56K as determined by sodium dodecyl sulfate polyacrylamine gel electrophoresis (SDS-PAGE). Similar results were obtained when the parasites were metabolically labeled with $^{35}$S-methionine. These data suggest that the molecule is a glycoprotein (Gp). When a total cell extract of $^3$H-glucosamine-labeled FVO proteins are separated by SDS-PAGE, it is clear that Gp56K is one of the major parasite glycoproteins. Resolution of the $^3$H-glucosamine-labeled glycoproteins from all six isolates on SDS-PAGE showed that the FVO and Geneva isolates both had a major glycoprotein of 56K. The other four isolates lacked Gp56K but had major glycoproteins of slightly lower molecular weight (approximately 50K).

To assess immunologically the relatedness of Gp50K and Gp56K, the antigens were immunoprecipitated with sera from two *Aotus* monkeys made immune to *P. falciparum* by repeated injections of the FVO isolate. The results using two such sera produced virtually identical results. The Gp56K from the FVO and Geneva isolates were clearly immunoprecipitated while Gp50K from the other isolates apparently was not recognized by the immune monkey sera from animals exposed to only FVO parasites. Either Gp56K or Gp50K in each of the isolates were bound by antibodies produced by immunizing monkeys with FVO and Honduras I/CDC parasites.

McAb (4-8-5D) produces a peripheral staining of both intracellular and extracellular merozoites by an IFAT. This type of fluorescence has been ascribed to antibody binding to surface antigens. However, unlike other McAb's which bound putative surface and intracellular antigens (Hall et al., (1983), supra,; Holder and Freeman, (1982), supra.,), and which immunoprecipitated multiple polypeptides, McAb 4-8-5D bound no other major constituent of *P. falciparum* besides Gp56K. The immunoprecipitation of a single (glyco)polypeptide by McAb 4-8-5D together with the immunoelectron microscopic data which demonstrates the extension of this molecule into the aqueous environment surrounding the cell indicated that Gp56K itself must be a component of the merozoite coat and/or plasma membrane.

The glycoproteins of the invention can be labeled in various ways, including $^{35}$S-methionine labeling and $^{3}$H-glucosamine labeling. $^{35}$S-methionine labelling was used to identify six proteins of approximate molecular weights of 202K, 185K, 142K, 136K, 82K and 46K, and $^{3}$H-glucosamine labeling was used to identify five glycoproteins of approximate molecular weights of 185K, 88K, 56K, 46K and 34K. The glycoprotein from FVO parasites of $M_r$ 56K was labeled with $^{3}$H-glucosamine and $^{3}$H-mannose, but not detectably labeled with $^{35}$S-methionine, $^{3}$H-fucose, or the sialic acid precursor $^{3}$H-N-acetyl mannosamine. The classification of this antigen as being a glycoprotein was based on its sensitivity to pronase treatment and that it could be labelled with $^{3}$H-glucosamine. The use of monoclonal antibodies has allowed isolation of this antigen and clear demonstration that it can be labeled with $^{35}$S-methionine. In addition, it has allowed purified glucosamine labeled Gp56K to be treated with glycosidases to show that the $^{3}$H-glucosamine had been incorporated into sugar side-chains as a monosaccharide, not into amino acids. This firmly establishes the molecule as a glycoprotein. The use of monoclonal antibodies showed that this antigen could be labeled with $^{35}$S-methionine and, therefore, was a glycoprotein.

The fact that the isolates with which McAb 4-8-5D did not react lack the 56K glycoprotein but contain major glycoproteins of 50K suggests homology between the 56K and 50K glycoproteins. For all isolates tested, each one has either the 50K or the 56K glycoprotein. Further evidence of the homology between these two glycoproteins is their isoelectric points. They are two of the most acidic glycoproteins made by the parasite, with an isoelectric point around 5.5. Most other glycoproteins have isoelectric points closer to neutrality.

The hybridoma which produces McAb 4-8-5D is on deposit with the American Type Culture Collection as ATCC HB 8938, on Nov. 25, 1985. The American Type Culture Collection (ATCC) is located at 12301 Parklawn Drive, Rockville, MD 20852.

What is claimed is:

1. A hybridoma cell line that produces monoclonal antibodies that bind to a merozoite surface glycoprotein of approximate molecular weight 56,000 that is present in the Geneva and FVO isolates of *Plasmodium falciparum*, said hybridoma cell line having the ATCC accession number HB 8938.

2. Monoclonal antibodies produced by the hybridoma cell line having the ATCC accession number HB 8938, said monoclonal antibodies binding to a merozoite surface glycoprotein of approximate molecular weight 56,000 that is present in the Geneva and FVO isolates of *Plasmodium falciparum*.

* * * * *